(12) United States Patent
Van den Heuvel (10) Patent No.: US 9,056,204 B2
(45) Date of Patent: Jun. 16, 2015

(54) UNIVERSAL IMPLANT

(75) Inventor: Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 1116 days.

(21) Appl. No.: 12/915,890

(22) Filed: Oct. 29, 2010

(65) Prior Publication Data

US 2012/0109297 A1 May 3, 2012

(51) Int. Cl.
*A61F 2/18* (2006.01)
*A61N 1/36* (2006.01)

(52) U.S. Cl.
CPC .................. *A61N 1/36032* (2013.01)

(58) Field of Classification Search
USPC ...................... 607/55–56, 136–137
See application file for complete search history.

(56) References Cited

U.S. PATENT DOCUMENTS

| | | | |
|---|---|---|---|
| 6,039,685 A | 3/2000 | Bushek | |
| 6,325,755 B1 | 12/2001 | Bushek et al. | |
| 6,482,144 B1 | 11/2002 | Muller | |
| 6,786,860 B2 | 9/2004 | Maltan et al. | |
| 2002/0032401 A1 | 3/2002 | Fereira et al. | |
| 2003/0031336 A1 | 2/2003 | Harrison et al. | |
| 2007/0055321 A1* | 3/2007 | Gordon et al. | 607/55 |
| 2010/0317913 A1 | 12/2010 | Conn et al. | |
| 2011/0034755 A1 | 2/2011 | Parker | |

FOREIGN PATENT DOCUMENTS

| | | |
|---|---|---|
| WO | WO 01/91678 | 12/2001 |
| WO | WO 2004/024212 | 3/2004 |
| WO | WO 2006/081361 | 1/2006 |
| WO | WO 2009/117767 | 3/2009 |
| WO | WO 2010/008630 | * 1/2010 |

OTHER PUBLICATIONS

Extended European Search Report, European Application No. 09798353.0, mailed Apr. 5, 2011 (5 pages).
International Search Report, International Application No. PCT/US2009/038893, mailed Jun. 11, 2009 (1 page).
Written Opinion, International Application No. PCT/US2009/038893, mailed Jun. 11, 2009 (6 pages).

* cited by examiner

*Primary Examiner* — Carl H Layno
*Assistant Examiner* — Jennifer Ghand
(74) *Attorney, Agent, or Firm* — Lowe Hauptman & Ham, LLP (57) ABSTRACT

A universal implant for an implantable medical device, the universal implant including a plurality of functional components, having a plurality of hardware components disposed in a housing, and an auxiliary component interface disposed in a surface of the housing and configured to electrically connect any one of a plurality of auxiliary components to the hardware components. The universal implant further includes a determinator configured to identify one or more of the auxiliary components, select one or more of the functional components based on the identified auxiliary components, and adapt the selected functional components for operation with the identified auxiliary components.

21 Claims, 9 Drawing Sheets

UNIVERSAL IMPLANT

BACKGROUND

1. Field of the Invention

The present invention relates generally to implantable medical devices, and more particularly, to a universal implant for an implantable medical device.

2. Related Art

Medical devices having one or more implantable components, generally referred to herein as implantable medical devices, have provided a wide range of therapeutic benefits to patients (sometimes referred to herein as recipients) over recent decades. Included among implantable medical devices are active implantable medical devices (AIMDs), which are medical devices having one or more implantable components that rely for their functioning upon a source of power other than the human body or gravity, such as an electrical energy source. AIMDs often include an implantable, hermetically sealed electronics module, and a device that interfaces with the patient, sometimes referred to herein as a patient interface. The patient interface may be a device that interfaces with a patient's tissue, sometimes referred to as a tissue interface. The tissue interface may, for example, diagnose, monitor, and/or treat a disease or injury, or to modify a patient's anatomy or to modify a physiological process of a patient.

For example, an AIMD tissue interface may include one or more conductive electrical contacts, referred to as electrode contacts, which deliver electrical stimulation signals to, or receive signals from, a patient's tissue. The electrode contacts are typically disposed in a biocompatible electrically non-conductive carrier, and are electrically connected to the electronics module. The electrodes and the non-conductive member are collectively referred to herein as an electrode assembly. As another example, an AIMD tissue interface may include a mechanical transducer that delivers stimulation to patient by vibrating tissue of the patient. As yet another example, the patient interface may include a transducer that indirectly interacts with a patient's tissue by, for example, providing acoustic signals to a patient.

The patient interface and electronics modules of AIMDs are generally manufactured together. As such, the electronics module of the AMID is generally manufactured for operation with a particular permanently connected patient interface.

SUMMARY

In one aspect of the present invention, a universal implant for an implantable medical device is disclosed. The universal implant comprises a plurality of functional components, including a plurality of hardware components disposed in a housing and an auxiliary component interface disposed in a surface of the housing and configured to electrically connect any one of a plurality of auxiliary components to said hardware components. The universal implant further comprises a determinator configured to identify one or more of the auxiliary components, select one or more of said functional components based on the identified auxiliary components, and adapt said selected functional components for operation with the identified auxiliary components.

In another aspect of the present invention, a kit comprising a plurality of auxiliary components and a universal implant is disclosed. The universal implant comprises a plurality of functional components, including a plurality of hardware components disposed in a housing, and an auxiliary component interface disposed in a surface of the housing configured to electrically connect any one of said plurality of auxiliary components to said hardware components. The universal implant further comprises a determinator configured to identify one or more of said auxiliary components, select one or more of said functional components based on the identified auxiliary components, and adapt said selected functional components for operation with said identified auxiliary components.

In yet another aspect of the invention, a method for operating a universal implant including a plurality of functional components is disclosed. The method comprises identifying one or more auxiliary components electrically connectable to said functional components, selecting one or more of the plurality of functional components for operation with the identified auxiliary components, wherein the selection is based on the identified auxiliary components, and adapting the selected functional components for operation with the identified auxiliary components.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a universal implant for an implantable medical device configured to operate any of one or more auxiliary components connectable to the universal implant. The universal implant comprises a plurality of functional components, including hardware components disposed in a housing, and an auxiliary component interface disposed on the housing configured to electrically connect any one of the auxiliary components to the hardware components. The universal implant also includes a determinator configured to identify one or more of the auxiliary components, select one or more of the functional components based on the identified auxiliary components, and adapt the selected functional components for operation with the identified auxiliary components. Advantageously, embodiments of the universal implant may be implemented as generic electronics modules for a plurality of different types of implantable medical devices. As such, the universal implant will enable greater commonality in the production of various types of implantable medical devices and thus allow greater efficiency to be achieved in the manufacture of various types of implantable medical devices.

Typically, different types of implantable medical devices are manufactured independently using separate production lines. As one example, cochlear implants and middle-ear implants are two types of implantable hearing prosthesis that are typically manufactured on separate production lines. As an additional example, a combination implantable hearing prosthesis that includes both a cochlear implant electrode assembly and a middle-ear implant transducer may conventionally be manufactured on a separate production line from cochlear implants and middle-ear implants. A universal implant in accordance with embodiments of the present invention may serve as the electronics module for any one of a plurality of different types of hearing prostheses, including each of the hearing prostheses mentioned above. As such, a single production line for manufacturing universal implants in accordance with embodiments of the present invention may replace a significant portion of each of the production lines of various conventional hearing prostheses. In this way, the production lines of conventional hearing prostheses may be significantly merged such that separate production lines may only be used to manufacture application-specific components of conventional hearing prostheses, such as the various patient interfaces for different types of hearing prostheses.

Exemplary embodiments of the present invention are described herein with reference to one class of implantable medical devices, namely, implantable hearing prostheses. It would be appreciated that a universal implant in accordance with embodiments of the present invention may be used as a generic electronics module for other types of implantable medical devices as well.

Figure 1:
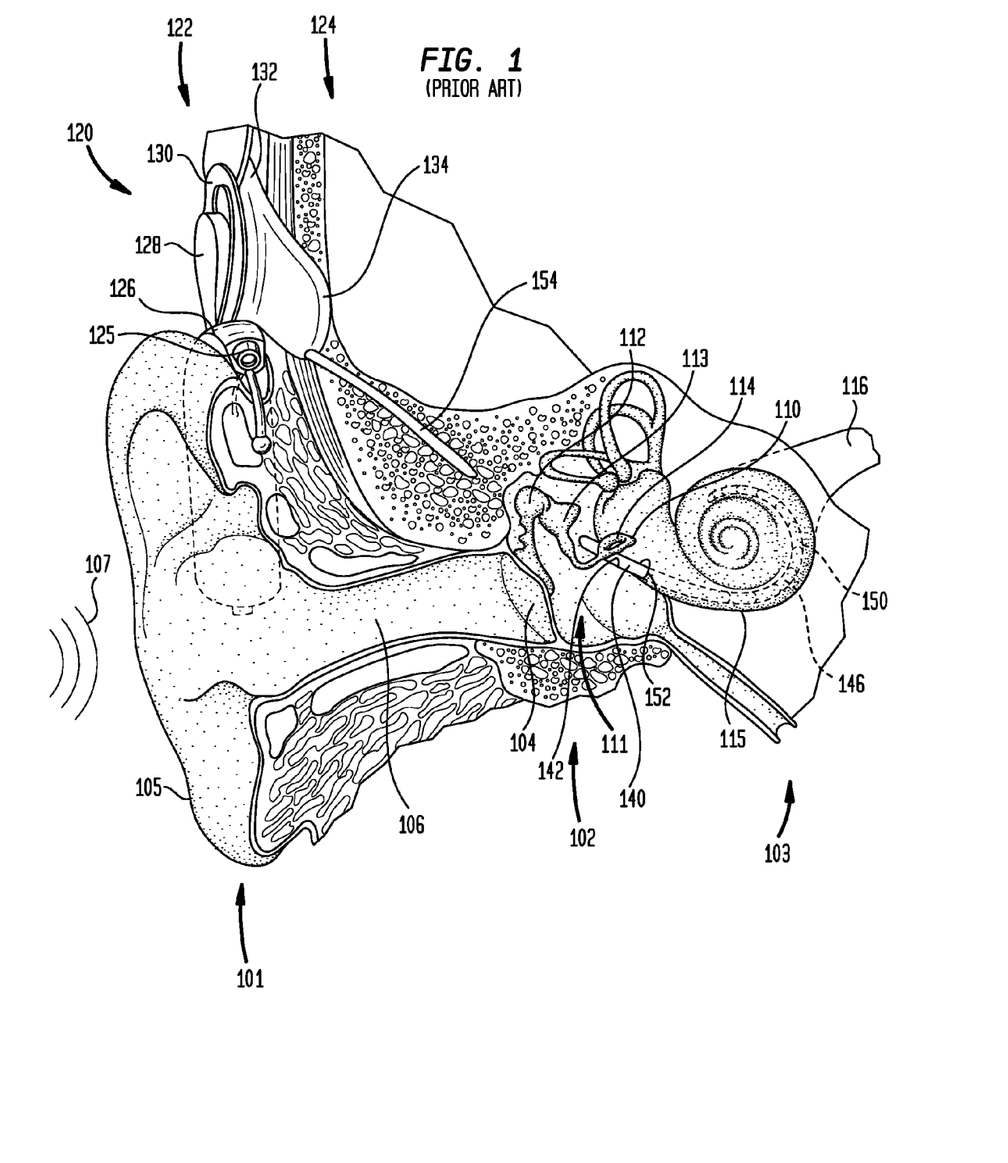
FIG. 1 illustrates one example of a conventional cochlear implant having a dedicated electronics module manufactured to operate the attached cochlear implant electrode assembly.

FIG. 1 illustrates one example of a conventional cochlear implant having a dedicated electronics module manufactured to operate the attached cochlear implant electrode assembly. In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In certain profoundly deaf persons, there is an absence or destruction of the hair cells. Cochlear implants, such a cochlear implant 120, are utilized to directly stimulate the ganglion cells to provide a hearing sensation to the recipient.

FIG. 1 also illustrates the positioning of cochlear implant 120 relative to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises microphone 125 for detecting sound which is output to a behind-the-ear (BTE) speech processing unit 126 that generates coded signals which are provided to an external transmitter unit 128, along with power from a power source (not shown) such as a battery. External transmitter unit 128 comprises an external coil 130 and, preferably, a magnet (not shown) secured directly or indirectly in external coil 130.

In the exemplary cochlear implant illustrated in FIG. 1, internal component assembly 124 comprises an internal coil 132 of a stimulator unit 134 that receives and transmits power and coded signals received from external assembly 122 to other elements of stimulator unit 134 which apply the coded signal to cochlea 115 via an implanted electrode assembly 140. Connected to stimulator unit 134 is a flexible cable 154. Flexible cable 154 electrically couples stimulator unit 134 to electrode assembly 140. Electrode assembly 140 comprises a carrier member 142 having one or more electrodes 150 positioned on an electrode array 146. Electrode assembly 140 enters cochlea 115 at cochleostomy region 152 and is positioned such that electrodes 150 are substantially aligned with portions of tonotopically-mapped cochlea 115. Signals generated by stimulator unit 134 are typically applied by the array 146 of electrodes 150 to cochlea 115, thereby stimulating auditory nerve 116. Electrode assembly 140 of cochlear implant 120 is permanently connected to stimulator unit 134 at the time of manufacture, and stimulator unit 134 is manufactured to be a dedicated electronics module for operating electrode assembly 140.

As noted above, cochlear implant 120 is one type of implantable hearing prosthesis. Other types of hearing prostheses include bone conduction devices, middle-ear implants, acoustic hearing aids, etc. Bone conduction devices utilize the bones of an individual's skull to transmit acoustic signals to the cochlea. Generally, most bone conduction hearing aids function by converting a received sound signal into vibration. This vibration is then transferred to a bone of a patient, the bone being the patient's skull in one particular embodiment. This skull vibration results in motion of the fluid of the cochlea, thereby stimulating the cochlear hair cells and causing the perception of sound in the patient. Middle ear implants also generally function by converting a received sound signal into vibration. However, middle ear implants transfer the vibration directly to a portion of the patient's middle ear, such as one of the three bones of the patient's middle ear (i.e., ossicles 111). In contrast, acoustic hearing aids receive ambient sound, amplify the sound, and direct the amplified sound into the ear canal. The amplified sound reaches the cochlea and causes motion of the cochlea fluid (perilymph), thereby stimulating the hair cells in the cochlea.

Generally, each type of hearing prosthesis is manufactured with an electronics module configured specifically to operate an attached patient interface. As such, different types of implantable hearing prostheses are generally manufactured independently using separate production lines. Embodiments of the present invention are generally directed to a universal implant for an implantable medical device configured to operate any of one or more auxiliary components connectable to the universal implant. As used herein, a "universal implant" is an electronics module for an implantable medical device configured to operate any of one or more auxiliary components connectable to the universal implant. As described above, universal implants in accordance with embodiments of the present invention may allow production lines for conventional hearing prostheses to be significantly merged.

Figure 2A:
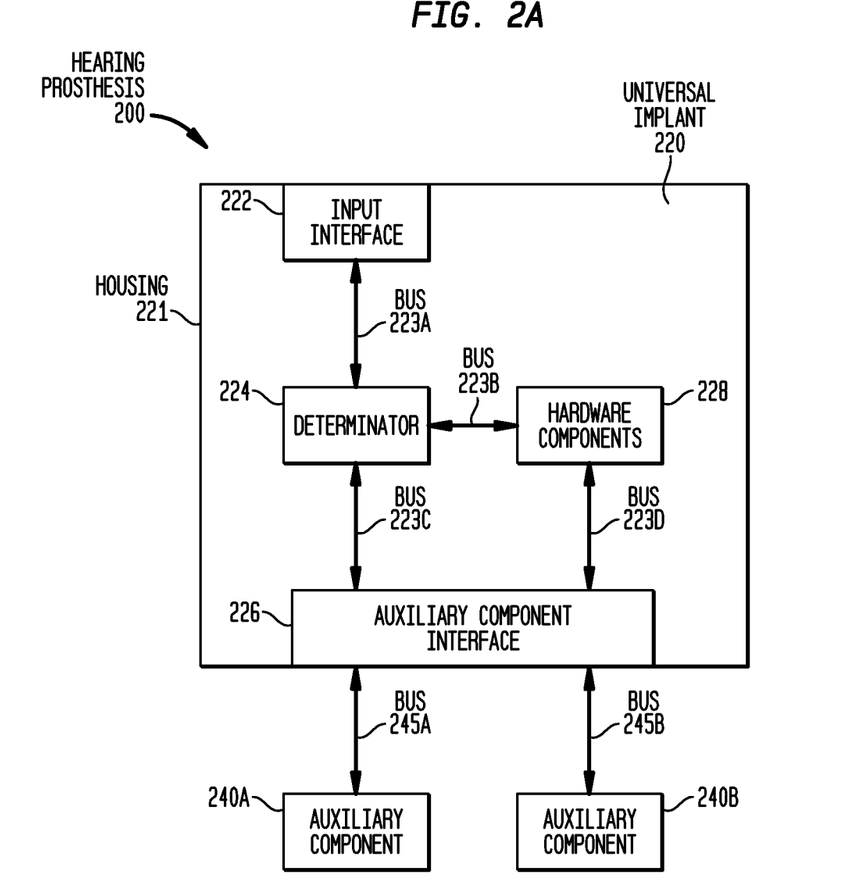
FIG. 2A is a functional block diagram of one embodiment of an implantable hearing prosthesis including a universal implant in accordance with embodiments of the present invention.

A functional block diagram of one embodiment of an implantable hearing prosthesis 200 including a universal implant 220, in accordance with embodiments of the present invention, is shown in FIG. 2A. As used herein, an "implantable hearing prosthesis" is a hearing prosthesis having one or more implantable components. Implantable hearing prosthesis 200 includes a universal implant 220 electrically connected to auxiliary components 240A and 240B. Universal implant 220 includes an input interface 222, a determinator 224, an auxiliary components interface 226, a housing 221 and functional components such as hardware components 228. In certain embodiments, the functional components of a universal implant may also include one or more software modules, as will be described further below. As used herein, a "functional component" is any component utilized to operate or drive an auxiliary component during operation of the universal implant, or any component or software utilized by those components. Determinator 224 and hardware components 228 are each disposed within housing 221. In certain embodiments, auxiliary component interface 226 and input interface 222 are disposed in the surface of housing 221, such that they are accessible from outside of housing 221. In alternative embodiments, one or more of auxiliary component interface 226 and input interface 222 may be disposed completely inside of housing 221. In such embodiments, a portion of the housing may be removable to allow access to one or more interfaces disposed within the housing.

In the embodiment illustrated in FIG. 2A, universal implant 220 is connected to two auxiliary components 240A and 240B. In accordance with embodiments of the present invention, universal implant 220 may be connected to one auxiliary component or more than two auxiliary components. As shown in FIG. 2A, auxiliary components 240A and 240B are electrically connected to auxiliary component interface 226 by buses 245A and 245B, respectively. Each of buses 245A and 245B may include one or more lines, and may include the same or a different number of lines. As used herein, an "auxiliary component" is any component that may be electrically connected to and operated by a universal implant of an AIMD. For example, an auxiliary component may be a patient interface for any type of implantable hearing prosthesis. Examples of such patient interfaces include any type of cochlear implant electrode assembly, such as a conventional-length electrode assembly, a short electrode assembly, a thin electrode assembly, an extra-cochlear electrode assembly, an endosteal electrode assembly, etc. Other examples of a patient interface include a transducer for use with a middle ear implant (a "middle ear implant transducer" herein), a transducer for use with a bone conduction implant (a "bone conduction implant transducer" herein), a transducer for use with an acoustic hearing aid (an "acoustic hearing aid transducer" herein), and any other type of transducer or other tissue interface for use as part of an implantable hearing prosthesis. In addition to patient interfaces, an auxiliary component may be any other type of component that may supplement a universal implant of an AIMD. Examples of such supplementary components include input components (e.g., external or implantable microphones, telecoils, etc.), communication components (e.g., inductive coils, capacitive data transfer elements) sensors, implantable power supplies, implantable transceivers, implantable processors, etc.

Figure 3:
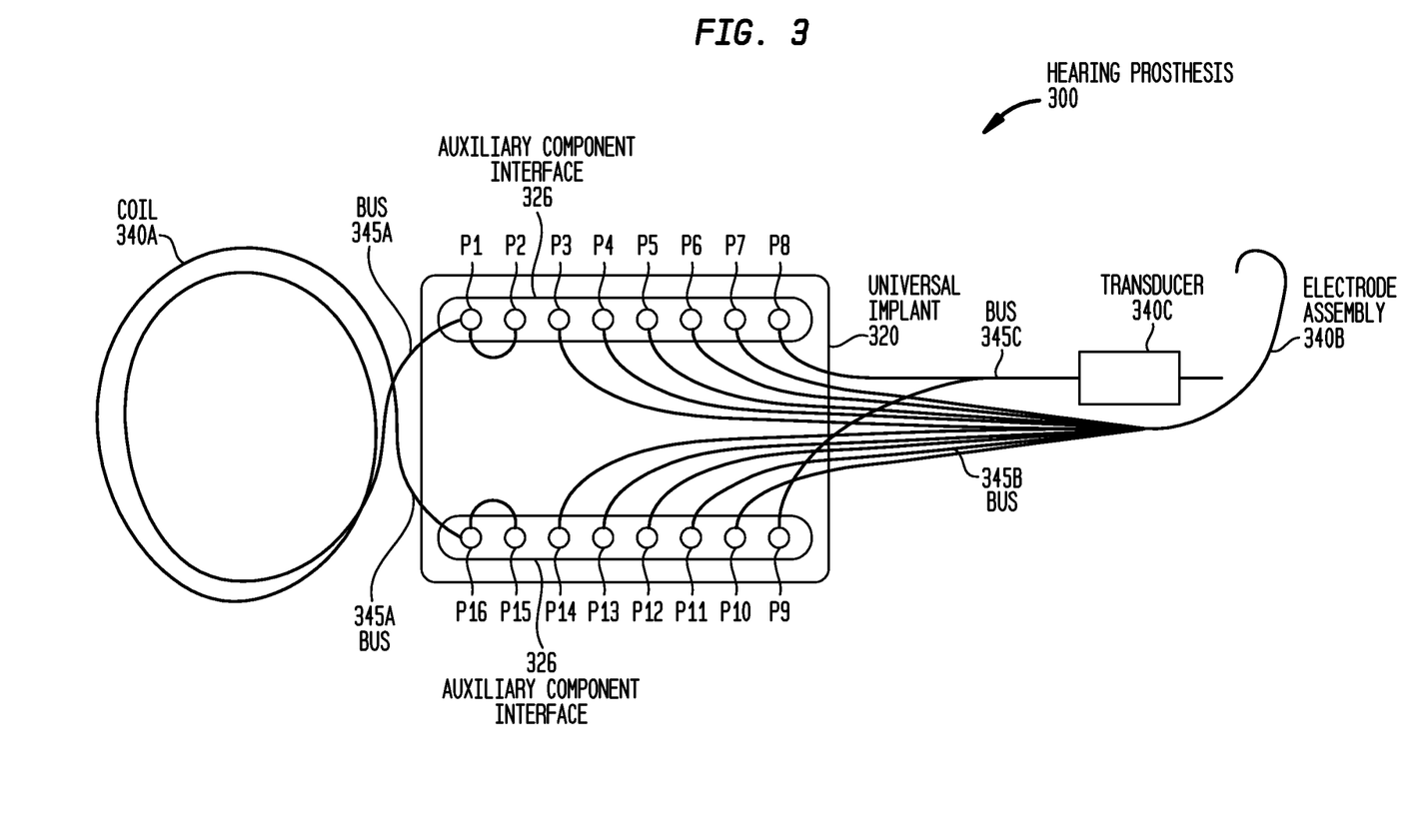
FIG. 3 is a schematic diagram of an implantable hearing prosthesis comprising a universal implant that includes an auxiliary component interface having a plurality of pins, in accordance with embodiments of the present invention.

In certain embodiments, auxiliary component interface 226 may comprise a plurality of pins to which buses 245A and 245B of auxiliary components 240A and 240B may be connected. A schematic diagram of one embodiment of an implantable hearing prosthesis 300 comprising a universal implant 320 that includes an auxiliary component interface 326 having a plurality of pins, in accordance with embodiments of the present invention, is shown in FIG. 3. In certain embodiments, universal implant 320 is similar to universal implant 220 described above, including an input interface 222, a determinator 224, hardware components 228 and an auxiliary component interface 326. Auxiliary component interface 326 of universal implant 320 includes a plurality of pins P1-P16. In other embodiments, auxiliary component interface 326 may include more or fewer pins than the number shown in FIG. 3. In certain embodiments, the pins may be feedthrough pins. A portion of the housing of universal implant 320 may be removable to allow access to the feedthrough pins. In the embodiment illustrated in FIG. 3, three auxiliary components 340A, 340B and 340C are electrically connected to universal implant 320 via pins P1-P16 of auxiliary component interface 326. More specifically, an inductive coil 340A is electrically connected by bus 345A to pins P1, P2, P15 and P16, a cochlear implant electrode assembly 340B is electrically connected by bus 345B to pins P3-P7 and P10-P14, and a middle ear implant transducer 340C is electrically connected by bus 345C to pins P8 and P9. The exemplary pin connections illustrated in FIG. 3 are schematic in nature and auxiliary components may be connected to pins of auxiliary component interface 326 in other configurations. In accordance with embodiments of the present invention, each of auxiliary components 340A, 340B and 340C may be electrically connected to a greater or lesser number of pins.

As discussed above, universal implant 220 comprises a determinator 224. Determinator 224 is electrically connected to auxiliary component interface 226 by a bus 223C. As will be described in further detail below with reference to FIGS. 2B and 2C, determinator 224 is configured to identify one or more auxiliary components for operation with universal implant 220, select one or more functional components for operation with universal implant 220 based the identified auxiliary components, and adapt the selected functional components for operation with the identified auxiliary components.

In the embodiment illustrated in FIG. 2A, determinator 224 is electrically connected to input interface 222 by a bus 223A. In certain embodiments, a user, such as a recipient, surgeon or clinician, may provide inputs to universal implant 220 through input interface 222. Input interface 222 configured to provide received inputs to determinator 224 via bus 223A. In accordance with embodiments of the present invention, input interface 222 is configured such that a user may enter inputs in one or more of a plurality of different ways. For example, in certain embodiments, a user may enter inputs by manipulating mechanical controls, such as one or more buttons, dials, switches, etc., of input interface 222. Alternatively or in addition, input interface 222 may be configured to receive vocal or other audio instructions. In certain embodiments, input interface may be configured to receive inputs via a remote control or an external component that is physically connected to input interface 222. Input interface may also receive inputs generated by an external system, such as a hearing prosthesis fitting system. In some embodiments, input interface 222 may be configured to physically or wirelessly connect to a docking station and receive inputs from the docking station. In accordance with embodiments of the present invention, inputs may be entered into input interface 222 by one or more of the methods described above. Input interface 222 may also receive input via any other presently known or later developed method.

Figure 2B:
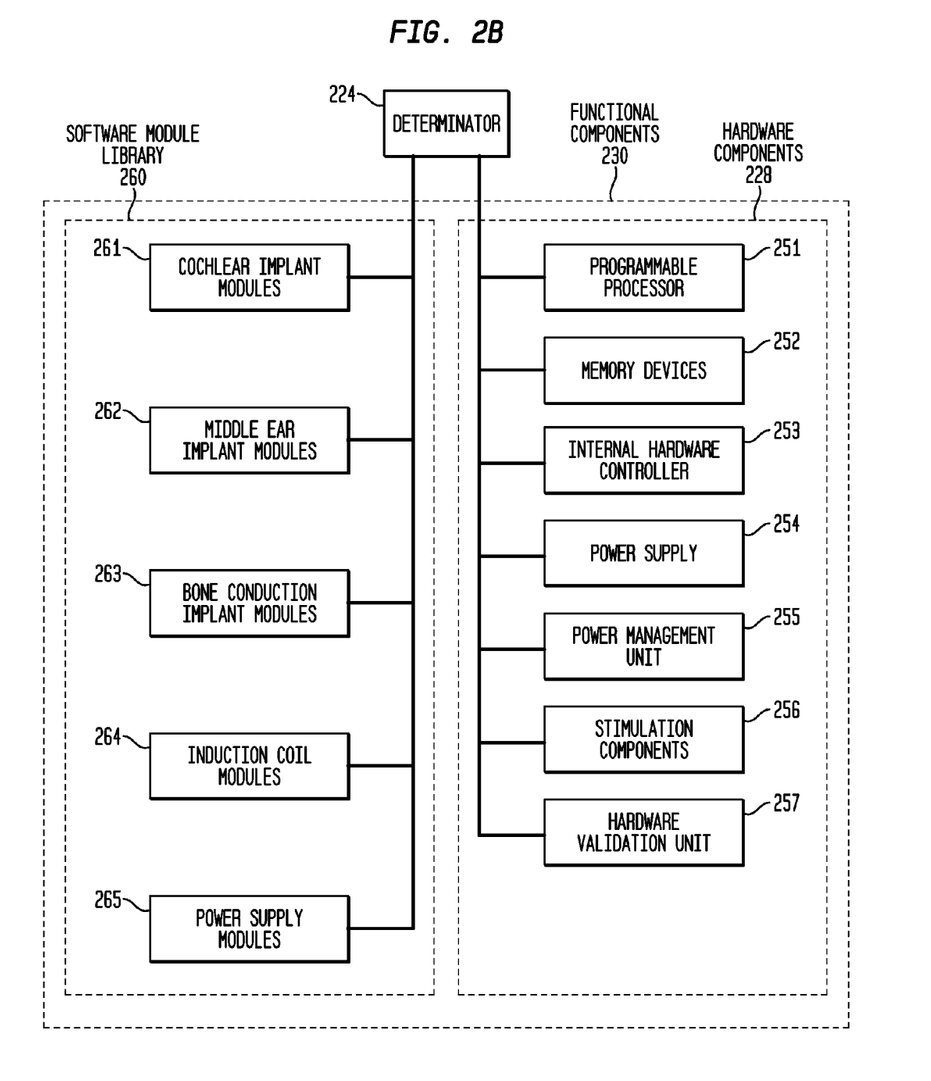
FIG. 2B is a schematic diagram illustrating functional components accessible to a determinator of a universal implant in accordance with embodiments of the present invention.

FIG. 2B is a schematic diagram illustrating functional components 230 that are accessible to determinator 224 in accordance with embodiments of the present invention. In the embodiment illustrated in FIG. 2B, components 230 that are accessible to determinator 224 include hardware components 228 and a software module library 260. In the embodiment illustrated in FIG. 2A, determinator 224 may be connected to hardware components 228 by a bus 223B. As illustrated in FIG. 2B, hardware components 228 may include a programmable processor 251, memory devices 252, an internal hardware controller 253, a power supply 254, a power management unit 255, stimulation components 256 and a hardware validation unit 257. In certain embodiments, hardware components 228 may include fewer hardware components, more hardware components, alternate hardware components, or any combination thereof, relative to hardware components 228 illustrated in FIG. 2B. In addition, the actual connections among the various hardware components 228 are not shown in FIG. 2B. Rather, FIG. 2B illustrates schematically exemplary hardware components 228 that are connected to determinator 224 directly or indirectly. Interactions between determinator 224, hardware components 228 and software module library 260 will be described below with reference to FIGS. 4A-4D.

In the embodiment illustrated in FIG. 2A, a bus 223D electrically connects auxiliary component interface 226 to hardware components 228. In other embodiments, auxiliary component interface 226 is electrically connected to hardware components 228 via determinator 224 and not through a separate bus 223D. In accordance with embodiments of the present invention, each of buses 223A-223D may include one line or a plurality of parallel lines, and each bus may have a different number of lines, or one or more of the buses may have the same number of lines. In certain embodiments, hardware components 228 are connected to auxiliary component interface 226 through a switching unit controlled by determinator 224. In such embodiments, determinator 224 uses the switching unit to selectively connect one or more of hardware components 228 to auxiliary component interface 226 and to one or more auxiliary components through auxiliary component interface 226.

Figure 4A:
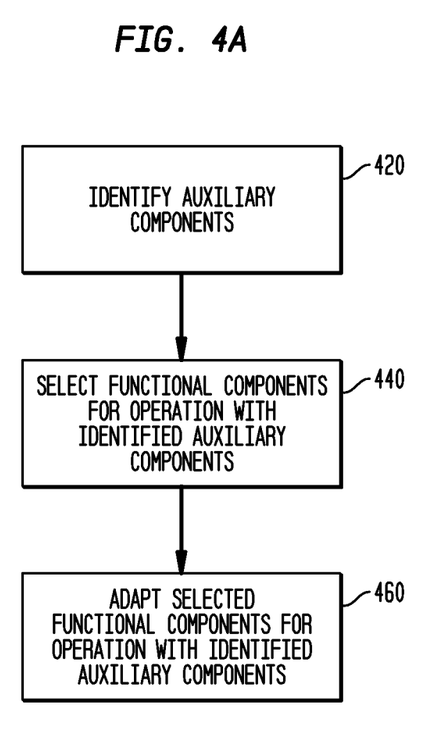
FIG. 4A is high-level a flowchart illustrating the operation of a universal implant in accordance with embodiments of the present invention.

FIG. 4A is high-level a flowchart illustrating the operation of a universal implant in accordance with embodiments of the present invention. The flowchart of FIG. 4A will be described in relation to the embodiments illustrated in FIGS. 2A-3. However, universal implants of other embodiments of the present invention may also be operated in accordance with the flowchart of FIG. 4A. At block 420, universal implant 220 identifies auxiliary components that are electrically connectable to hardware components 228. In certain embodiments, universal implant 220 identifies, at block 420, auxiliary components that are to be operated by universal implant 220. Multiple methods of identifying auxiliary components at block 420, in accordance with embodiments of the present invention, are described below with reference to FIGS. 4B and 4C.

As described above, in certain embodiments of the present invention, auxiliary component interface 226 of universal implant 220 may comprise a plurality of pins to which auxiliary components may be electrically connected. A schematic diagram of one such embodiment is shown in FIG. 3, which illustrates a universal implant 320 comprising an auxiliary component interface 326 including a plurality of pins P1-P16. In certain embodiments, the pins of universal implant 320 have static pin designations. As used herein, a universal implant including pins having "static pin designations" is configured such that each pin, or each unique grouping of the pins, is designated by the universal implant for operation with only one type of auxiliary component. In certain embodiments, for example, pins P1-P16 of universal implant 320 may have static pin designations in which pins P1, P2, P15 and P16 are designated for operation with inductive coils, pins P3-P7 and P10-P14 are designated for operation with cochlear implant electrode assemblies, and pins P8 and P9 are designated for operation with middle ear implant transducers.

Figure 4B:
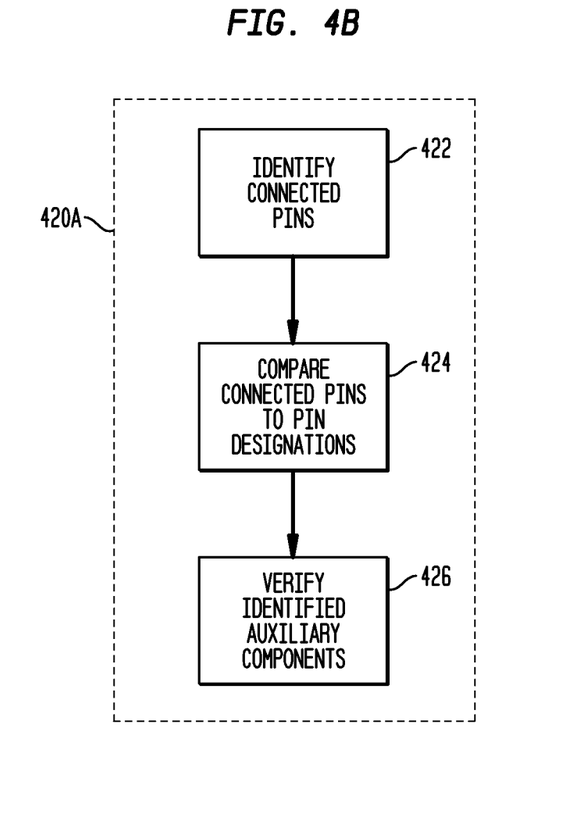
FIG. 4B is a flowchart illustrating the identification of auxiliary components electrically connected to a universal implant having pins with static pin designations, in accordance with embodiments of the present invention.

FIG. 4B is a flowchart illustrating the identification of auxiliary components electrically connected to a universal implant 320 having pins with static pin designations, in accordance with embodiments of the present invention. Block 420A of FIG. 4B contains a flowchart illustrating one procedure for identifying auxiliary components at block 420 of FIG. 4A in accordance with embodiments of the present invention. In embodiments in which the pins of universal implant 320 have static pin designations, determinator 224 may identify what auxiliary components are connected to universal implant 320 by identifying which pins of auxiliary component interface 326 are presently connected to an auxiliary component. As such, in some embodiments, after connecting one or more auxiliary components to pins of auxiliary component interface 326, determinator 224 of universal implant 320 identifies, at block 422, all of the pins of auxiliary component interface 326 to which an auxiliary component is presently connected. A pin to which an auxiliary component is presently connected may be referred to herein as a "connected pin".

After identifying the connected pins at block 422, determinator compares the connected pins to the static pin designations at block 424 to identify what auxiliary components are connected to universal implant 320. For example, in the embodiment of universal implant 320 in which pins P3-P6 and P11-P14 are designated for operation with cochlear implant electrode assemblies. In that embodiment, if determinator 224 detects that one or more of pins P3-P6 and P11-P14 is a connected pin, determinator 224 will identify a cochlear implant electrode assembly as an auxiliary component presently connected to universal implant 320. However, if determinator 224 detects that none of pins P3-P6 and P11-P14 is a connected pin, then determinator will not identify a cochlear implant electrode assembly as an auxiliary component presently connected to universal implant 320. Additionally, in the same embodiment of universal implant 320 described above, pins P1, P2, P15 and P16 are designated for operation with inductive coils. As such, if determinator 224 detects that one or more of pins P1, P2, P15 and P16 is a connected pin, then determinator 224 will identify an inductive coil as a connected auxiliary component. However, if determinator 224 detects that none of pins P1, P2, P15 and P16 is a connected pin, then determinator will not identify an inductive coil as an auxiliary component presently connected to universal implant 320. Determinator 224 will make a similar determination with regard to a middle-ear implant transducer using pins P8 and P9. In accordance with embodiments of the present invention, determinator 224 may determine whether a pin is a connected pin by checking the impedance of the pin or a line connected to the pin, or by any other currently known or later developed method.

At block 426, determinator 224 verifies that the auxiliary components identified on the basis of the static pin designations of universal implant 320 were correctly identified. This verification may be performed by evaluating characteristics of the identified auxiliary components through the connected pins. For example, if determinator 224 has identified a cochlear implant electrode assembly as being connected to pin P3, determinator 224 may use any method now known or later developed to confirm that a cochlear implant electrode assembly is in fact electrically connected to pin P3. For example, determinator 224 may compare the impedance of a line connected to pin P3 with an expected impedance if a cochlear implant electrode assembly were connected to pin P3. If the identified auxiliary components are successfully verified at block 426, then the universal implant proceeds to block 440 of FIG. 4A. However, if the verification at block 426 is not successful, then the universal implant may provide an appropriate indication to a recipient, surgeon, clinician or other user and not proceed to block 440. In certain embodiments, block 426 may be omitted.

In other embodiments of the present invention, auxiliary component interface 226 of universal implant 220 comprises a plurality of pins, but universal implant 220 does not have static pin designations. In such embodiments, an auxiliary component may be connected to any collection of pins of auxiliary component interface 226 provided there are enough pins available to connect to that auxiliary component. Pins without static pin designations may be referred to herein as "programmable pins".

Figure 4C:
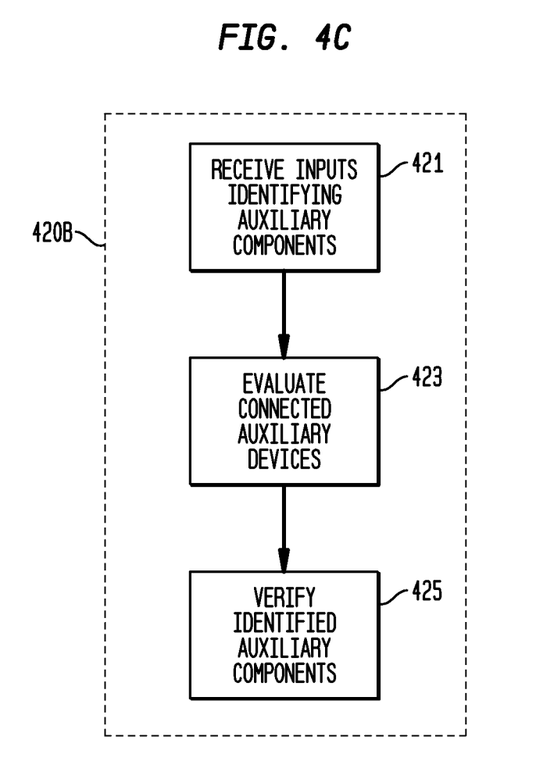
FIG. 4C is a flowchart illustrating the identification of auxiliary components electrically connectable to hardware components of a universal implant not having static pin designations, in accordance with embodiments of the present invention.

FIG. 4C is a flowchart illustrating the identification of auxiliary components electrically connectable to hardware components 228 of a universal implant 220 not having static pin designations, in accordance with embodiments of the present invention. Block 420B of FIG. 4C contains a flowchart illustrating one procedure for identifying auxiliary components at block 420 of FIG. 4A. At block 421 of FIG. 4C, universal implant 220 receives inputs identifying certain auxiliary components that are electrically connectable to hardware components 228. In certain embodiments, at block 421, universal implant 220 receives inputs identifying auxiliary components that have been or will be connected to hardware components 228 for operation of the identified auxiliary components. Universal implant 220 may receive inputs at block 421 in a number of different ways. In certain embodiments, a user, such as a recipient, surgeon or clinician, may enter inputs to universal implant 220 identifying the auxiliary components via input interface 222. In such embodiments, the inputs may be entered via one or more of mechanical controls, audio instructions, a remote control or other external component, a docking station, etc., as described above in relation to input interface 222. Input interface 222 is configured to provide the received inputs to determinator 224. In addition, inputs may be received at block 421 before or after connecting auxiliary components to universal implant 220.

After connecting auxiliary components to universal implant 220, determinator 224 evaluates the connected auxiliary components at block 423 to determine what auxiliary components are connected to universal implant 220, independent of the inputs received at block 421. Determinator 224 may use any method now known or later developed to determine what auxiliary components are connected to universal implant 220. For example, determinator 224 may compare the impedance of a line connected to one of the auxiliary components to a bank of expected impedances to determine what auxiliary component is connected to universal implant 220. At block 425, determinator 224 verifies that the auxiliary components identified via the inputs received at block 421 are consistent with the auxiliary components determined at block 423 to be connected to universal implant 220. If the identified auxiliary components are successfully verified at block 425, then universal implant 220 proceeds to block 440 of FIG. 4A. However, if the verification at block 425 is not successful, then universal implant 220 may provide an appropriate indication to a recipient, surgeon, clinician or other user and not proceed to block 440. In other embodiments, block 425 may be omitted.

In some embodiments, identifying auxiliary components at block 420 of FIG. 4A may omit receiving inputs at block 421 and verifying the identified auxiliary components at block 425. In other embodiments, identifying auxiliary components at block 420 of FIG. 4A may omit evaluating connected auxiliary components at block 423 and verifying the identified auxiliary components at block 425. In still other embodiments, determinator 224 may evaluate connected auxiliary components before receiving user inputs and then prompt a user to confirm, by entering inputs via input interface 222 for example, the identifications made by determinator 224.

The flowchart of FIG. 4C has been described above in relation to a universal implant 220 having an auxiliary component interface 226 including a plurality of pins. However, identifying auxiliary components, as described in relation to FIG. 4C, may also be implemented by embodiments of universal implant 220 in which auxiliary component interface 226 provides an interface for electrically connecting auxiliary components that does not include pins.

After identifying auxiliary components at block 420 of FIG. 4A, universal implant 220 selects one or more of functional components 230 for operation with the identified auxiliary components at block 440. In some embodiments of the present invention, universal implant 220 includes functional components that may be used with one or more auxiliary components, but are not used with every auxiliary component electrically connectable to universal implant 220. As such, in certain embodiments, determinator 224 selects one or more of functional components 230 based on the identified auxiliary components.

Examples of selecting one or more of functional components 230 at block 440 will now be described with reference to FIG. 2B. In certain embodiments of the present invention, determinator 224 may store internally an indication of which of functional components 230 to select based on the identified auxiliary components. Alternatively, determinator 224 may retrieve from one of memory devices 252 a file indicating which of functional components 230 to select for operation with identified auxiliary components.

In the embodiment illustrated in FIG. 2B, functional components 230 include stimulation components 256 among hardware components 228. Among stimulation components 256 are stimulation components for operation with various types of patient interfaces. For example, stimulation components 256 may include components, such as capacitors, used to generate the electrical stimulation applied to a recipient through a cochlear implant electrode assembly. Stimulation components 256 may also include components used to generate mechanical stimulation, such as vibrations, applied to a recipient through a middle ear implant transducer or a bone conduction implant transducer. When the only auxiliary device electrically connected to universal implant 220 is a cochlear implant electrode assembly, for example, determinator 224 may select the stimulation components for operation with a cochlear implant electrode assembly, but not select the stimulation components used to generate mechanical stimulation for a middle-ear implant transducer or a bone conduction implant transducer. Alternatively, if one of the auxiliary components is a middle ear implant transducer, then the stimulation components for a that type of transducer may be selected. If both a cochlear implant electrode assembly and a middle ear implant transducer are identified auxiliary components, then determinator 224 may select stimulation components configured to operate with the cochlear implant electrode assembly and stimulation components configured to operate with a middle-ear implant transducer.

Additionally, when operating certain auxiliary components it may be desirable to implement power management functions to extend the life of implantable power supplies, while such power management is less important when operating other auxiliary components. As such, determinator 224 may also select power management unit 255 if such power management is desirable when operating any one of the identified auxiliary components.

In certain embodiments, determinator 224 selects one or more hardware components of universal implant 220 by using a switching unit, such as a switch matrix, to electrically connect the one or more hardware component to the identified auxiliary components. In certain embodiments, determinator 224 controls the connections made by the switching unit. In the embodiment illustrated in FIG. 2A, the switching unit connects one or more hardware components to the identified auxiliary components via auxiliary component interface 226. In some embodiments, the switching unit is electrically connected between hardware components 228 and bus 223D. In embodiments in which auxiliary component interface 226 comprises a plurality of pins for connection to auxiliary components, auxiliary component interface 226 may connect one or more lines of bus 223D to the pins of auxiliary component interface 226.

Alternatively or in addition, determinator 224 may select the one or more hardware components by connecting the one or more hardware components to a power supply or by leaving the hardware component connected to the power supply if it is already connected. Similarly, in some embodiments, determinator 224 may disconnect non-selected hardware components from a power supply. As described above, functional components of universal implant 220 also include a software module library 260 that is accessible to determinator 224 in the embodiment illustrated in FIG. 2B. In certain embodiments of the invention, selecting functional components for operation with identified auxiliary components, at block 440, includes selecting one or more software modules to be loaded onto one or more of the selected hardware components.

At block 460 of FIG. 4A, determinator 224 adapts the selected functional components of universal implant 220 for operation with the identified auxiliary components. As noted above, the selected functional components may include one or more selected hardware components and one or more selected software modules. Certain hardware components of universal implant 220 function in the same way for various different auxiliary components, while the characteristics of other hardware components must be adapted to operate with particular auxiliary components. For example, the sound processing required to operate a cochlear implant electrode assembly is different than the sound processing required to operate a middle-ear implant or a bone conduction implant. As such, a processor capable of performing sound processing functions may need to be adapted to function with the identified auxiliary components to be operated by the universal implant. In certain embodiments, determinator 224 adapts at least one of the functions and characteristics of one or more hardware components for operation with the identified auxiliary components.

In some embodiments of the present invention, determinator 224 is configured to adapt at least one of the functions and characteristics of one or more hardware components of universal implant 220 in a number of different ways. In some embodiments, determinator 224 may adapt a selected hardware component for operation with an identified auxiliary component by loading software stored in a software module library onto the hardware component. In the embodiment illustrated in FIG. 2B, universal implant 220 has access to a software module library 260 including software modules for each type of auxiliary component that may be operated by universal implant 220. FIG. 2B schematically illustrates a software module library 260 that is accessible to determinator 224. In certain embodiments, software module library 260 may be stored in one or more of memory devices 252. Alternatively, software module library 260 may be stored wholly or partially outside of universal implant 220, such as on a docking station, fitting system, or other external component that may be physically or wirelessly connected to universal implant 220.

In the embodiment illustrated in FIG. 2B, software module library 260 includes cochlear implant electrode assembly software modules 261, middle ear implant transducer software modules 262, bone conduction implant transducer software modules 263, induction coil software modules 264 and power supply software modules 265. In other embodiments, software module library 260 may include fewer software modules, more software modules, alternate software modules, or any combination thereof, relative to the software modules illustrated in FIG. 2B. An example in which determinator 224 adapts selected hardware components for operation with a cochlear implant electrode assembly will be described below.

Figure 2C:
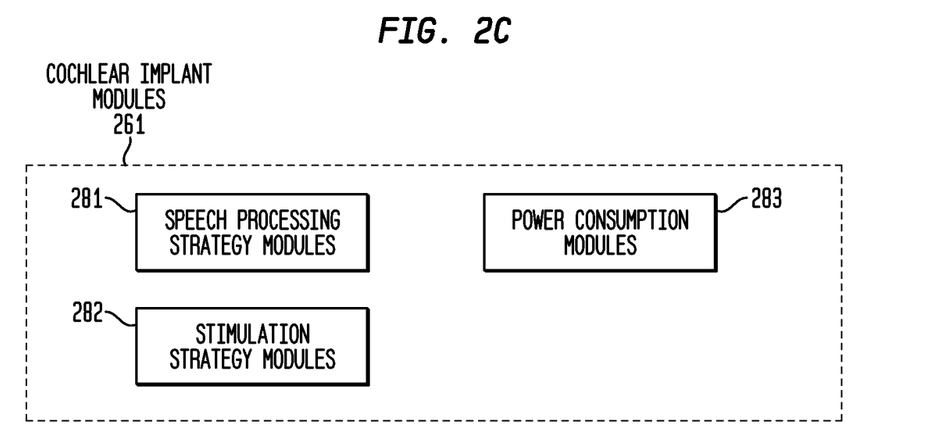
FIG. 2C schematically illustrates a plurality of cochlear implant electrode assembly software modules in accordance with embodiments of the present invention.

When one of the identified auxiliary components is a cochlear implant electrode assembly, determinator 224 may load one or more of cochlear implant electrode assembly modules 261 onto one or more of the selected hardware components of universal implant 220. FIG. 2C schematically illustrates a plurality of cochlear implant electrode assembly software modules 261 in accordance with embodiments of the present invention. In the embodiment illustrated in FIG. 2C, cochlear implant electrode assembly software modules 261 include speech processing strategy modules 281, stimulation strategy modules 282 and power consumption modules 283. In other embodiments, cochlear implant electrode assembly software modules 261 may include fewer software modules, more software modules, alternate software modules, or any combination thereof, relative to the software modules illustrated in FIG. 2C.

When operating a cochlear implant electrode assembly to provide a recipient with hearing precepts, a speech processing strategy may be implemented by universal implant to perform at least a portion of the processing required to convert ambient sound into electrical stimulation signals for application by the cochlear implant electrode assembly. In certain embodiments, the speech processing strategy may be implemented by programmable processor 251, which determinator 224 may select at block 440 of FIG. 4A. To adapt programmable processor 251 for operation with a cochlear implant electrode assembly at block 460, determinator 224 may load one of speech processing strategy modules 281 onto programmable processor 251 so that programmable processor 251 will implement the speech processing strategy specified by that module. Speech processing strategy modules 281 may include a plurality of software modules implementing different speech processing strategies for a cochlear implant electrode assembly. A user may specify, via input interface 222, the speech processing strategy to be loaded by determinator 224, or determinator 224 may select the speech processing strategy independent of user inputs.

In certain embodiments, universal implant 220 also implements a stimulation strategy specifying how to apply generated stimulation signals to the recipient. The stimulation strategy may be implemented by one or more cochlear implant stimulation components selected from stimulation components 256, internal hardware controller 253 and programmable processor 251. To adapt these components to implement the stimulation strategy, determinator 224 may load one of stimulation strategy modules 282 onto one or more of the selected cochlear implant stimulation components, internal hardware controller 253 and programmable processor 251. In some embodiments, determinator 224 will also customize power management unit 255 at block 460 by loading one of power consumption modules 283 onto power management unit 255 so that power management unit 255 will implement the power management strategy specified by the loaded power consumption module.

Figure 4D:
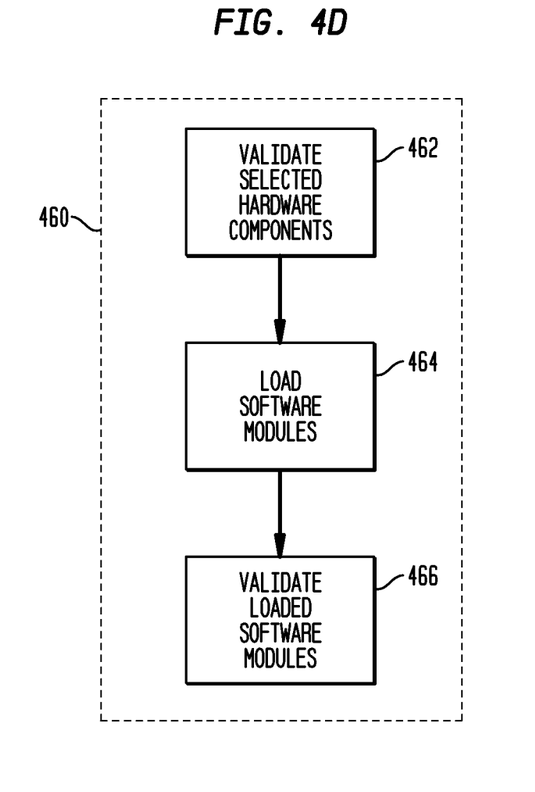
FIG. 4D is a flowchart illustrating one way of adapting the selected functional components for operation with identified auxiliary components in accordance with embodiments of the present invention.

FIG. 4D is a flowchart illustrating one way of adapting the selected functional components for operation with the identified auxiliary components in accordance with embodiments of the present invention. Block 460 of FIG. 4D contains a flowchart illustrating one procedure for adapting of selected functional components for operation at block 460 of FIG. 4A, in accordance with embodiments of the present invention. At block 462 of FIG. 4D, determinator 224 validates the selected hardware components to ensure that these components are operating properly. Validation of the selected hardware components may be performed using known hardware validation techniques. In certain embodiments, determinator 224 may utilize hardware validation unit 257 to validate operation of the selected hardware components. At block 464, determinator 224 loads software modules onto one or more of the selected hardware components, as described above in relation to the exemplary software modules of FIG. 2C. Determinator 224 then validates the loaded software modules using conventional software testing techniques at block 466. If either of the verifications at blocks 462 and 466 are not successful, then universal implant 220 may provide an appropriate indication to a recipient, surgeon, clinician or other user. In other embodiments, one or more of the hardware and software validations of blocks 462 and 466 may be omitted.

In some embodiments of the present invention, the software modules of software module library 260 are executable programs that are loaded onto one or more selected hardware components and that are configured to implement all of the functions needed to operate a particular auxiliary component. In other embodiments, certain hardware components have generic executable programs that may be supplemented by the software modules of software module library 260 to provide the generic program with additional functions used in the operation of a particular auxiliary component.

While adapting the selected hardware components for operation with identified auxiliary components has been described above for an embodiment in which a cochlear implant electrode assembly is the identified auxiliary component, determinator 224 may adapt the selected functional components for operation with any other type of auxiliary components in a similar way, in accordance with embodiments of the invention. For example, in certain embodiments, software module library 260 includes one or more software modules for each auxiliary component that may be operated by universal implant 220. When adapting the selected functional components for operation with a particular auxiliary components, determinator 224 may load one or more selected software modules corresponding to that auxiliary component onto one or more selected hardware modules as described above in relation to a cochlear implant electrode assembly.

For example, if the identified auxiliary component is a middle-ear implant transducer, determinator 224 may load one or more of middle-ear implant transducer modules 262 onto one or more selected hardware components, such as a selected speech processing strategy and a selected stimulation strategy. As another example, if the identified auxiliary component is an induction coil, determinator 224 may load one or more of induction coil modules 264 onto one or more selected hardware components for operation of the induction coil. In certain embodiments, when adapting selected functional components for operation at block 460, determinator 224 may load one or more software modules received via input interface 222 onto one or more selected hardware components.

In certain embodiments of the present invention, multiple identified auxiliary components may be connected to universal implant for operation at the same time. In such embodiments, determinator 224 loads software modules corresponding to each of the identified auxiliary components onto one or more selected hardware components. In some embodiments, the auxiliary components may each require one or more software modules to be loaded onto the same hardware components. For example, if a cochlear implant electrode assembly and a middle ear implant transducer are both connected to universal implant 220, then universal implant 220 must implement a different speech processing for each of these auxiliary components. In some embodiments, both speech processing strategies may be implemented on programmable processor 251. In such embodiments, programmable processor 251 may have a generic executable program, as described above, and determinator 224 may supplement this program with a cochlear implant electrode assembly software module and a middle ear implant transducer software module to provide programmable processor 251 with functions for operating both the electrode assembly and the transducer. In other embodiments, universal implant may include multiple programmable processors 251, and determinator 224 may load a cochlear implant electrode assembly software module into one of the programmable processors and may load a middle ear implant transducer software module into another one of the programmable processors.

In some embodiments, determinator 224 may also be configured to modify characteristics of one or more of the hardware components of universal implant 220 at block 460. For example, one or more of hardware components 228 may be implemented as application-specific integrated circuits (ASICs) or other types of integrated circuits (ICs). In certain embodiments, determinator 224 is configured to adjust characteristics of the ASICs or ICs based on the identified auxiliary components. Determinator 224 may adjust the ASICs or ICs based on information specific to each auxiliary component stored in software module library 260. As used herein, "adapting" functional components for operation includes one or more of loading software onto one or more hardware components, changing one or more parameters or characteristics of one or more hardware components, or otherwise adjusting the operation of one or more hardware components. In alternative embodiments, hardware components of the universal implant may be configured to select and run the appropriate software for the identified auxiliary components upon receiving from the determinator an indication of which auxiliary components are the identified auxiliary components.

In addition to adapting selected functional components for operation with identified auxiliary components, determinator 224 may also adapt universal implant 220 to suit a particular recipient's needs. For example, in response to inputs received via input interface 222, determinator 224 may adapt universal implant 220 for a recipient's needs by loading software onto one or more of hardware components 228, adjusting characteristics of one or more hardware components 228, or both. As one example, determinator 224 may load a specified speech processing strategy onto a processor of hardware components 228 in response to inputs received via input interface 222. As noted above, inputs received via input interface 222 may be entered by one or more of a user (such as a surgeon, clinician or recipient) a fitting system, docking station, remote control, etc.

In accordance with embodiments of the present invention, auxiliary components may be physically and electrically connected to the universal implant after manufacture of the universal implant. For example, one or more auxiliary components may be physically and electrically connected to a universal implant before or during a surgical procedure to implant the universal implant in a recipient. For example, one or more auxiliary components may be physically and electrically connected to a universal implant after the separate manufacture of the universal implant and the auxiliary components. As another example, an auxiliary component may be physically and electrically connected to the universal implant during a subsequent surgical procedure after the initial implantation of the universal implant in the recipient. As such, embodiments of the invention advantageously allow auxiliary components to be added or replaced after initial implantation of the universal implant, without the need to remove the universal implant, re-implant the universal implant, or implant a new electronics module. For example, a universal implant connected to a middle ear implant as an auxiliary component may be implanted in a recipient to treat the recipient's hearing loss. However, over time the recipient's hearing may deteriorate further such that the recipient may benefit more from a cochlear implant than a middle ear implant. A universal implant in accordance with embodiments of the invention would allow a surgeon to replace the middle ear implant with a cochlear implant without having to remove the universal implant, which may reduce the amount of surgery required for such a procedure as compared to performing the same procedure when a device that is permanently connected to one or more auxiliary components was initially implanted. A universal implant in accordance with embodiments of the invention may also be adapted for operation with one or more auxiliary components, as described above, before, during or even after a surgical procedure to implant the universal implant in a recipient.

In addition, a universal implant in accordance with embodiments of the present invention may be used by a surgeon or other user without requiring the user to have detailed knowledge of the operation of the universal implant. For example, in certain embodiments, the user may be able to configure the universal implant by merely indicating, using an input interface, what auxiliary components have been or will be connected to the universal implant. In other embodiments, a user need only connect one or more auxiliary components to the device, and determinator will adapt the device for operation, as described above, without further input from the user.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive.

What is claimed is:

1. A universal implant for an implantable medical device, the universal implant comprising: a plurality of functional components, including a plurality of hardware components disposed in a housing; an auxiliary component interface disposed in a surface of the housing and configured to electrically connect any one of a plurality of auxiliary components to said hardware components; an input interface configured to receive input pertaining to a selected auxiliary component; and a determinator coupled to the input interface configured to select one or more of said functional components at least partially based on the received input from the input interface pertaining to the selected auxiliary component, and adapt said selected functional components for operation with the selected auxiliary component based on the selection of the one or more said functional components.

2. The universal implant of claim 1, wherein the auxiliary component interface comprises a plurality of pins.

3. The universal implant of claim 1, wherein, when one or more of the auxiliary components is electrically connected to the auxiliary component interface, the determinator is configured to evaluate and identify the electrically connected auxiliary components.

4. The universal implant of claim 1, wherein said selected functional components include one or more software modules and one or more selected hardware components of said plurality of hardware components, and wherein said determinator is configured to load each of said software modules onto one or more of said selected hardware components to adapt the selected functional components for operation with the selected auxiliary component.

5. A kit comprising: a plurality of auxiliary components; and a universal implant comprising: a plurality of functional components, including a plurality of hardware components disposed in a housing; an auxiliary component interface disposed in a surface of the housing and configured to electrically connect at least one of said plurality of auxiliary components to said hardware components; an input interface configured to receive input indicating that the at least one auxiliary component is or will be connected to the auxiliary component interface; and a determinator coupled to the input interface configured to select one or more of said functional components and adapt said selected functional components for operation with the at least one auxiliary component based on the input received by the input interface.

6. The kit of claim 5, wherein said functional components further include a software module library including one or more software modules for each of the auxiliary components.

7. The kit of claim 6, wherein the plurality of auxiliary components comprises two or more of a cochlear implant electrode assembly, a middle-ear implant transducer, a bone conduction implant transducer, an induction coil and an auxiliary power supply, and wherein a software module library includes one or more software modules for each of a cochlear implant electrode assembly, a middle-ear implant transducer, a bone conduction implant transducer, an induction coil and an auxiliary power supply.

8. The kit of claim 5, wherein said selected functional components include one or more software modules for the at least one auxiliary component and one or more selected hardware components of said plurality of hardware components, and wherein the determinator is configured to load each of said software modules onto one or more of said selected hardware components to adapt said selected functional components for operation with the at least one auxiliary component.

9. The kit of claim 8, wherein the determinator is further configured to adjust one or more parameters of one or more of said hardware components to adapt said selected functional components for operation with the least one auxiliary component.

10. A method for operating a universal implant including a plurality of functional components, comprising:
   identifying one or more auxiliary components electrically connectable to said functional components;
   selecting one or more of the plurality of functional components for operation with the identified auxiliary components, wherein the selection is based on the identified auxiliary components; and
   adapting the selected functional components for operation with the identified auxiliary components,
   wherein the universal implant comprises an input interface, and wherein said identifying one or more auxiliary components electrically connectable to said functional components comprises:
   receiving inputs via the input interface; and
   identifying one or more auxiliary components electrically connectable to said functional components at least partially based on the received inputs.

11. The method of claim 10, wherein said identifying one or more auxiliary components electrically connectable to said functional components further comprises: evaluating auxiliary components electrically connected to the universal implant.

12. The method of claim 10, wherein said selected functional components include one or more selected hardware components, and wherein said adapting the selected functional components for operation with the identified auxiliary components comprises:
   selecting one or more software modules from a software module library at least partially based on the identified auxiliary components;
   receiving at least one of the selected software modules through the input interface; and
   loading each of the selected software modules onto one or more of the selected hardware components.

13. The method of claim 10, wherein said functional components include one or more hardware components, and wherein said selecting one or more of the plurality of functional components for operation with the identified auxiliary components comprises:
   adjusting a switching unit to electrically connect the one or more of the hardware components to an auxiliary component interface electrically connectable to the identified auxiliary components.

14. A universal implant for an implantable medical device, the universal implant comprising:
   a plurality of functional components, including a plurality of hardware components disposed in a housing;
   an auxiliary component interface disposed in a surface of the housing and configured to electrically connect any one of a plurality of auxiliary components to said hardware components; and
   a determinator configured to identify one or more of the auxiliary components, select one or more of said functional components based on the identified auxiliary components, and adapt said selected functional components for operation with the identified auxiliary components; and further comprising:
   an input interface disposed on the housing and configured to receive inputs and provide the received inputs to the determinator, wherein
   the determinator is configured to identify the one or more of the auxiliary components at least partially based on the received inputs.

15. The universal implant of claim 14, wherein the input interface is configured to receive one or more of mechanically entered inputs, audio inputs, electrical inputs from an external device, or wirelessly communicated inputs.

16. The universal implant of claim 14, wherein, when one or more of the auxiliary components is electrically connected to the auxiliary component interface, the determinator is configured to evaluate and identify the electrically connected auxiliary components.

17. The universal implant of claim 14, wherein said selected functional components include one or more software modules and one or more selected hardware components of said plurality of hardware components, and wherein said determinator is configured to load each of said software modules onto one or more of said selected hardware components to adapt the selected functional components for operation with the identified auxiliary components.

18. The universal implant of claim 14, wherein said functional components further include a software module library including one or more software modules for each of the auxiliary components.

19. The universal implant of claim 14, wherein the plurality of auxiliary components comprises two or more of a cochlear implant electrode assembly, a middle-ear implant transducer, a bone conduction implant transducer, an induction coil and an auxiliary power supply, and wherein a software module library includes one or more software modules for each of a cochlear implant electrode assembly, a middle-ear implant transducer, a bone conduction implant transducer, an induction coil and an auxiliary power supply.

20. The universal implant of claim 14, wherein said selected functional components include one or more software modules for each of the identified auxiliary components and one or more selected hardware components of said plurality of hardware components, and wherein the determinator is configured to load each of said software modules onto one or more of said selected hardware components to adapt said selected functional components for operation with said identified auxiliary components.

21. The universal implant of claim 14, wherein the determinator is further configured to adjust one or more parameters of one or more of said hardware components to adapt said selected functional components for operation with said identified auxiliary components.

* * * * *